United States Patent [19]

Schmidt, Jr. et al.

[11] Patent Number: 4,526,577
[45] Date of Patent: Jul. 2, 1985

[54] DISPOSABLE ARTICLE CONSTRUCTIONS

[75] Inventors: Robert C. Schmidt, Jr., Port Murray; Paul P. Puletti, Glen Gardner, both of N.J.

[73] Assignee: National Starch and Chemical Corporation, Bridgewater, N.J.

[21] Appl. No.: 569,001

[22] Filed: Jan. 9, 1984

[51] Int. Cl.$^3$ .......................... A61F 13/16; B32B 7/14
[52] U.S. Cl. .................................. 604/366; 156/291; 156/327; 428/198; 428/200; 428/517; 604/370; 604/372; 604/373
[58] Field of Search ............... 604/365, 370, 373, 366, 604/372; 428/198, 200, 517

[56] References Cited

U.S. PATENT DOCUMENTS

| | | |
|---|---|---|
| 3,239,478 | 3/1966 | Harlan . |
| 3,700,633 | 10/1972 | Wald . |
| 3,837,994 | 9/1974 | Flanagan . |
| 3,917,607 | 11/1975 | Crossland . |
| 3,932,327 | 1/1976 | Korpman . |
| 4,147,580 | 4/1979 | Buell ................................. 156/291 |
| 4,205,679 | 6/1980 | Repke et al. ...................... 604/366 |
| 4,212,910 | 7/1980 | Taylor et al. ........................ 428/35 |
| 4,299,745 | 11/1981 | Godfrey . |
| 4,419,494 | 12/1983 | Puletti et al. ...................... 525/95 |
| 4,460,728 | 7/1984 | Schmidt et al. .................... 604/370 |

OTHER PUBLICATIONS

Stereon 840A In Hot Melt Pressure Sensitive Adhesives from Firestone Kraton Thermoplastic Rubber from Shell 9/81.

*Primary Examiner*—James C. Cannon
*Attorney, Agent, or Firm*—Edwin M. Szala; Ellen T. Dec

[57] ABSTRACT

Styrene-butadiene block copolymers are used as hot melt bonding agents in the formation of disposable laminates by using multi-line adhesive application.

14 Claims, No Drawings

DISPOSABLE ARTICLE CONSTRUCTIONS

BACKGROUND OF THE INVENTION

The present invention relates to disposable articles prepared using multi-line construction and especially to multi-line disposable diaper, sanitary napkin and bed pad constructions and to hot melt adhesives useful for the assembly thereof.

While a wide range of uses for hot melt adhesive compositions are known throughout the disposable industry, it has been found that a hot melt adhesive used for bonding in a particular use or application may be completely unsuitable for other uses or applications. Thus, various hot melt adhesive compositions have been proposed for use in the construction of disposable articles. Depending upon the type of construction employed, the adhesive must possess certain physical properties. Perhaps the most stringent properties are those required of adhesives to be used in the bonding of polyethylene films, or the like, to tissue or non-woven substrates in the production of articles, particularly diapers, sanitary napkins and bed pads, using multi-line construction techniques. This class of disposable construction presents unique problems for the adhesive formulator. The adhesive must possess a high degree of adhesion since it is applied in the form of a number of very fine parallel longitudinal stripes thus requiring each line of adhesive to possess exceptionally high bonding properties. The adhesive must also possess sufficient adhesive and cohesive strength to provide high bond strength values when subjected to stress so the constructions cannot be easily separated. As an additional criteria, it is necessary that the adhesive, upon application, not absorb throughout the actual disposable construction and that the adhesive bonds not only remain secure but also be flexible even after prolonged periods of storage. In addition to requiring heat and oxidation resistance on aging they must also possess sufficient bonding range and must be white or clear in color.

To date, only hot melt adhesives based on ethylene vinyl acetate copolymers or on atactic polypropylene have been used for these multi-line constructions and neither of these approaches have resulted in adhesives possessing all the desirable properties discussed above. Thus, the polypropylene based adhesives have adequate adhesion requirements at the sacrifice of stability and bonding range while the ethylene vinyl acetate adhesives provide the flexibility while sacrificing adhesion and bond strength. Further, in order to formulate either type into adhesives which have the bonding range or open time required for these applications, it has been necessary to formulate them as semipressure sensitives which consequently has further reduced their cohesive strength resulting in loss of bonding during storage or transport at elevated temperatures.

While the term "multi-line" construction is used herein to represent the above-described embodiment, it will be understood that the term may also be used to include articles constructed using a "multi-dot" or "multi-stripe" pattern or application, i.e. any assembly requiring the use of a large number of adhesive deposits, each deposit being of a small quantity of adhesive.

It is therefore an object of the present invention to provide a hot melt adhesive composition suitable for use in the construction of multi-line disposable articles. It is a further object to provide hot melt pressure sensitive adhesive compositions which can be applied at relatively low temperatures and will retain their superior bonding strength even when subjected to prolonged periods of storage.

This and other objects will be apparent from the description that follows.

SUMMARY OF INVENTION

We have now found that pressure sensitive hot melt compositions prepared from A-B-A type block and multi-block copolymers are particularly useful in the construction of multi-line assembles.

Thus, the present invention is directed to a disposable article of the multi-line type construction comprising at least one polyethylene or polypropylene substrate bonded to at least one tissue, non-woven, polyethylene or polypropylene substrate using a hot melt pressure sensitive adhesive composition comprising:

(a) 15 to 35% by weight of an A-B-A block or multi-block copolymer where the B component is butadiene or hydrogenated butadiene;

(b) 45 to 70% by weight of a compatible tackifying resin;

(c) 5 to 30% by weight of a plasticizing oil;

(d) 0 to 5% by weight of a petroleum derived wax; and (e) 0.1 to 2% by weight of a stabilizer.

More particularly, the present invention is directed to the use of a hot melt adhesive composition especially adapted for the above described construction the hot melt adhesives containing as the block copolymer a multi-block styrene-butadiene copolymer containing at least 35 parts styrene per 100 parts copolymer.

DETAILED DESCRIPTION OF THE PREFERRED EMBODIMENTS

The primary component of the adhesive compositions used in the present invention are block or multi-block copolymers having the general configuration:

A-B-A or A-B-A-B-A-B- wherein the polymer blocks A are non-elastomeric polymer blocks which, as homopolymers have glass transition temperatures above 20° C., while the elastomeric polymer blocks B are butadiene or butadiene which is partially or substantially hydrogenated. Further, they may be linear or branched. Typical branched structures contain an elastomeric portion with at least three branches which can radiate out from a central hub or can be otherwise coupled together.

The non-elastomeric blocks which make up 14 to 86% by weight of the block copolymer may comprise homopolymers or copolymers of vinyl monomers such as vinyl arenes, vinyl pyridines, vinyl halides and vinyl carboxylates, as well as acrylic monomers such as acrylonitrile, methacrylonitrile, esters of acrylic acids, etc. Monovinyl aromatic hydrocarbons include particularly those of the benzene series such as styrene, vinyl toluene, vinyl xylene, ethyl vinyl benzene as well as dicyclic monovinyl compounds such as vinyl naphthalene and the like. Other non-elastomeric polymer blocks may be derived from alpha olefins, alkylene oxides, acetals, urethanes, etc. Styrene is preferred.

The elastomeric block component making up the remainder of the copolymer is butadiene which may or may not be hydrogenated as taught, for example, in U.S. Pat. No. 3,700,633. This hydrogenation may be either partial or substantially complete. Selected conditions may be employed for example to hydrogenate the elastomeric butadiene block while not so modifying the vinyl arene polymer blocks. Other conditions may be chosen to hydrogenate substantially uniformly along the polymer chain, both the elastomeric and non-elastomeric blocks thereof being hydrogenated to practically the same extent, which may be either partial or substantially complete.

Typical of the rubbery block copolymers useful herein are the polystyrene-polybutadiene-polystyrene, and e.g. polystyrene-poly-(ethylenebutylene)-polystyrene. These copolymers may be prepared using methods taught, for example, in U.S. Pat. Nos. 3,239,478; 3,427,269; 3,700,633; 3,753,936; and 3,932,327. Alternatively, some may be obtained from Shell Chemical Co. under the trademarks Kraton 1101, 1102, 1650, 1652 and 1657 and from Phillips Chemical Co. under the trademarks Solprene 418 and 423.

Most preferred for use herein are the linear A-B-A-B-A multi-block copolymers where the elastomeric block is butadiene and the non-elastomeric block is styrene and the latter is present in relatively high concentrations, i.e. at levels of 35% or above. Block copolymers marketed commercially at this time which meet the above described requirements are available from Firestone under the tradename Stereon 840A (57 parts butadiene and 43 parts styrene). Blends of these high styrene containing copolymers with other compatable block copolymers may also be employed.

The tackifying resins useful in the adhesive compositions can be hydrocarbon resins, synthetic polyterpenes, rosin esters, natural terpenes, and the like. More particularly, the useful tackifying resins include any compatible resins or mixtures thereof such as (1) natural and modified rosins such, for example, as gum rosin, wood rosin, talloil rosin, distilled rosin, hydrogenated rosin, dimerized rosin, and polymerized rosin; (2) glycerol and pentaerythritol esters of natural and modified rosins, such, for example as the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; (3) copolymers and terpolymers of natured terpenes, e.g. styrene/terpene and alpha methyl styrene/terpene; (4) polyterpene resins having a softening point, as determined by ASTM method E28-58T, of from about 80° to 150° C; the latter polyterpene resins generally resulting from the polymerization of terepene hydrocarbons, such as the bicyclic monoterpene known as pinene, in the presence of Friedel-Crafts catalysts at moderately low temperatures; also included are the hydrogenated polyterpene resins; (5) phenolic modified terpene resins and hydrogenated derivatives thereof such, for example, as the resin product resulting from the condensation, in an acidic medium, of a bicyclic terpene and a phenol; (6) aliphatic petroleum hydrocarbon resins having a Ball and Ring softening point of from about 70° to 135° C.; the latter resins resulting from the polymerization of monomers consisting of primarily of olefins and diolefins; also included are the hydrogenated aliphatic petroleum hydrocarbon resins; (7) aromatic petroleum hydrocarbon resins and the hydrogenated derivatives thereof; and (8) alicyclic petroleum hydrocarbon resins and the hydrogenated derivatives thereof. Mixtures of two or more of the above described tackifying resins may be required for some formulations.

The selection of the particular tackifying agent is, in large part, dependent upon the specific block copolymer employed. The preferred adhesive formulations for use herein which employ the linear multiblock Stereon type copolymers provide optimum properties when tackifiers of modified terpene having ring and ball softening point of about 100°–120° C. such as Zonatac 105 are employed.

Among the applicable stabilizers or antioxidants utilized herein are included high molecular weight hindered phenols and multifunctional phenols such as sulfur and phosphorous-containing phenols. Hindered phenols are well known to those skilled in the art and may be characterized as phenolic compounds which also contain sterically bulky radicals in close proximity to the phenolic hydroxyl group thereof. In particular, tertiary butyl groups generally are substituted onto the benzene ring in at least one of the ortho positions relative to the phenolic hydroxy group. The presence of these sterically bulky substituted radicals in the vicinity of the hydroxyl group serves to retard its stretching frequency and, correspondingly, its reactivity; this steric hindrance thus providing the phenolic compound with its stabilizing properties. Representative hindered phenols include: 1,3,5-trimethyl 2,4,6-tris (3,5-di-tert-butyl-4-hydroxybenzyl)benzene; pentaerythrityl tetrakis-3(3,5-di-tert-butyl-4-hydroxyphenyl)propionate; n-octadecyl-3(3,5-di-tert-butyl-4-hydroxyphenyl)-propionate; 4,4'-methylenebis (2,6-tert-butylphenol); 4,4'-thiobis (6-tert-butyl-o-cresol); 2,6-di-tertbutylphenol; 6-(4-hydroxyphenoxy)-2,4-bis(n-octylthio)-1,3,5triazine; di-n-octadecyl 3,5-di-tert-butyl-4-hydroxybenzylphosphonate; 2-(n-octylthio)ethyl 3,5-di-tert-butyl-4-hydroxybenzoate; and sorbitol hexa[3-(3,5-di-tert-butyl-4-hydroxyphenyl)propionate].

The performance of these antioxidants may be further enhanced by utilizing, in conjunction therewith known synergists such, for example, as thiodipropionate esters and phosphites, particularly useful is distearylthiodipropionate.

These stabilizers, if used, are generally present in amounts of about 0.1 to 1.5 weight percent, preferably 0.25 to 1.0%.

Various plasticizing or extending oils are also present in the composition in amounts of 5% to about 30%, preferably 5 to 25%, by weight in order to provide wetting action and/or viscosity control. The above broadly includes not only the usual plasticizing oils but also contemplates the use of olefin oligomers and low molecular weight polymers as well as vegetable and animal oil and their derivatives. The petroleum derived oils which may be employed are relatively high boiling materials containing only a minor proprotion of aromatic hydrocarbons (preferably less than 30% and, more particularly, less than 15% by weight of the oil). Alternatively, the oil may be totally non-aromatic. The oligomers may be polypropylenes, polybutenes, hydrogenated polyisoprene, hydrogenated polybutadiene, or the like having average molecular weights between about 350 and about 10,000. Vegetable and animal oils include glyceryl esters of the usual fatty acids and polymerization products thereof.

Various petroleum derived waxes may also be used in amounts less than about 15% by weight of the composition in order to impart fluidity in the molten condition of the adhesive and flexibility to the set adhesive, and to serve as a wetting agent for bonding cellulosic fibers. The term "petroleum derived wax" includes both paraffin and microcrystalline waxes having melting points within the range of 130°–225° F. as well as synthetic waxes such as low molecular weight polyethylene or Fisher-Tropsch waxes.

The adhesive compositions are prepared by blending the components in the melt at a temperature of about 130°–200° C. until a homogeneous blend is obtained, approximately 2 hours. Various methods of blending are known to the art and any method that produces a homogeneous blend is satisfactory.

The resultant adhesives are then used to bond polyethylene or polypropylene substrates to tissue, non-wovens or other polyethylene or polypropylene substrates using techniques involving multiple dispositions of small quantities of the adhesives according to conventional "multi-line" or "multi-dot" type constructions. Although the procedures used to manufacture these disposable constructions vary depending upon the particular manufacturer, the adhesive is generally extruded in lines (or dots) at regularly spaced intervals along the length of the article. The adhesive is usually applied to the polyethylene or polypropylene backing and subsequently the combination is mated with an absorbent inner core and tissue or non-woven liner.

This invention can be further illustrated by the following examples of preferred embodiments thereof, although it will be understood that these examples are included merely for purposes of illustration and are not intended to limit the scope of the invention unless otherwise specifically indicated.

Testing Procedures

End Seal Test: A polyethylene backsheet is bonded to a non-woven liner and a sample, 3 gluelines in width, cut therefrom. One end of the polyethylene is clamped into the jaws of a tensile tester held at a 180° angle and the corresponding end of the non-woven pulled similarly in the opposite direction. The force required to separate the bond is then recorded in grams. For the applications contemplated herein, it is desirable that values of at least about 300 grams be obtained. Such high degrees of bond strength are desired in the multi-line disposable assemblies in order to prevent the separation of the substrates. Adhesives conventionally utilized herein have produced constructions having end seal bond values of less than 200 grams and often only about 100 grams.

Adhesion Failure Temperature is a measure of the ability of the bond to withstand an elevated temperature rising at 5° F. every 15 minutes under a constant force which pulls the bond. In this test bonds 1 inch by 4 mm were formed of polyethylene onto Kraft paper and the force used to pull the bond kept constant at 25 grams. The test results are designated as Incremental Peel Pass/Fail values and show the transitional temperature range at which bond failure occurs. Adhesives possessing high failure temperatures are essential for these disposable constructions which are often subjected to very high temperature conditions during transport and/or storage.

Operating Window Test: Bonds are formed as in the Adhesion Failure Test. The application temperature of the glue is incrementally reduced until substrate failure did not occur either with fresh bonds or those aged 24 hours at room temperature. This minimum temperature is designated the minimum bonding temperature and is an indication of the lowest application temperature which will still give a good bond. Since the temperature at which the hot melt adhesive is used may vary throughout the actual manufacturing operation, an adhesive with a low minimum bonding temperature will be more versatile and will result in less down time and, consequently higher production rates.

Static Time to Failure Bond Test: Adhesive (held at 325° F.) was applied to a series of polyethylene surfaces ½ inch in width and a 1½ inch long and hand compressed onto similar size sheets of Kraft paper. The bonds were hung vertically with 50 gram weights and maintained at 105° F. The time to failure was noted. It should be noted with respect to this test that the results thereof will vary from one series of tests to another and therefore comparisons can be made only between samples tested at the same time.

This test is an indication of the heat resistance of the adhesive under temperature conditions approximating those encountered during use (wear) of the disposable construction. Long failure times are desirable indicating strong bonds which are particularly essential in certain areas of the disposable constructions which are subjected to greater stress during use.

Adhesive Strength: The adhesion to stainless steel and to Mylar (polyester) film was measured by peeling the tape backing over itself 180° at a constant speed (by a force applied to the free end of the tape) from a smooth steel surface or HDPE to which it has been applied by a fixed pressure. For the techniques used in conducting this test, see the 180° peel adhesion test PSTC-1 of the Pressure Sensitive Tape Council. This test can be performed only on adhesive formulations which are pressure sensitive and is a measure of the strength or tenacity of the adhesive.

EXAMPLE I

Ten parts white USP mineral oil and 0.1 parts Irganox 1010 antioxidants were blended with 20 parts Stereon 840A at 325° F. When the blend was homogeneous, 10 additional parts oil were added followed by 60 parts Zonatac 105 Lite, a modified terpene tackifier.

The resulting pressure sensitive ahesive (designated Adhesive A) exhibited a viscosity (Brookfield Thermosel Viscometer) of 1355 at 325° F. and 8060 at 250° F.

A similar adhesive (designated Adhesive B) was prepared using 60 parts Arkon M-100, a $C_9$ aromatic feedstream, as a tackifier.

Adhesives A and B were compared with two adhesives presently employed in the commercial production of multi-line diapers, one of which (Adhesive C) is based on a composition prepared from ethylene vinyl acetate, alpha-methyl styrene and styrene and another (Adhesive D) from a resin fortified atactic polypropylene.

Five samples of each of the four adhesives were then subjected to the Static Time to Failure Bond Test and observed at 15 minute intervals. The values for each test are shown in Table I.

| Adhesive | A | B | C (control) | D (control) |
|---|---|---|---|---|
| 1 | 2.5 hr. | 3.75 hr. | 15 min. | 15 min. |
| 2 | 3 hr. | 4 hr. | 15 min. | 30 min. |
| 3 | 3 hr. | 7 hr. | 15 min. | 30 min. |
| 4 | 3 hr. | 8 hr. | 15 min. | 30 min. |
| 5 | 3 hr. | >8 hr. | 15 min. | 30 min. |

As the results show, the heat resistance as measured in terms of the Static Time to Failure was many fold higher for the adhesives prepared using the compositions of the present invention.

The adhesives prepared above were then compared with the conventionally employed adhesives (including a third adhesive, adhesive E, prepared from ethylene vinyl acetate and terpene) by subjecting the adhesives to the Adhesion Failure and Operating Window tests described previously. The results are presented below:

| Adhesive | Peel Pass/Fail °F. | Mininum Bonding Temperature |
|---|---|---|
| Adhesive A | 135/140 | <200° F. |
| Adhesive B | 145/150 | Not tested |
| Adhesive C | 90/95 | 225° F. |
| Adhesive D | 105/110 | 275° F. |
| Adhesive E | 105/110 | 275° |

Again the Adhesives of the present invention gave results for superior to those obtained using the adhesives conventionally employed for these applications.

End seal tests were then run on a series of commercially produced multi-line diaper constructions bonded with Adhesives A, C and D. In the case of Adhesive D, the commercial diaper was bonded with bead widths of 0.065 inches. Consequently, for comparative purposes, D* is shown as indicative of end seal values normalized to the 0.0125 bead widths used in the commercial A and C constructions. Another commercially available diaper bonded with an alternate atactic polypropylene adhesive (Adhesive F) was also tested. In this case, the commercial diaper was prepared using bead widths of 0.04 inches. For comparison F* has been normalized to a 0.0125 bead width.

| Adhesive: | A | C | D | D* | F | F* |
|---|---|---|---|---|---|---|
|  | 500 | 40 | 800 | 160 | 240 | 75 |
|  | 480 | 16 | 800 | 160 | 280 | 88 |
|  | 400 | 22 | 660 | 132 | 220 | 69 |
|  | 380 | — | — | — | — | — |
| Bead Width (in): | .0125 | .0125 | .0625 | .0125 | .04 | .0125 |

The above results show the improved end seal strength obtained using the adhesives of the present invention. Thus, while diapers can be prepared with other conventional adhesives, it is seen from sample D) that acceptable strength values are obtained only when substantially larger amounts of adhesive are employed. The undesirable aspects of the use of these wider bead widths both with respect to aesthetics and quantity of adhesive used are apparent.

EXAMPLE II

Using the general procedure described in Example I, other adhesives were prepared using various block copolymers in place of the Stereon 840A. The adhesive compositions were subjected to the Adhesion Failure test, Adhesive Strength Test and Static Time to Failure test.

| Block Copolymer | Peel Pass/Fail °F. | Adhesive Strength | Static Time to Failure |
|---|---|---|---|
| Adhesive A | 135/140 | 8 pli | 7 hrs. |
| Kraton G1652 | 125/130 | 5 pli | >48 hrs. |
| Kraton 1102 | 115/120 | 7 pli | 8 hrs. |
| Kraton 1107 | 100/110 | 7 pli | 3 hrs. |

As seen from the above results, while the adhesive strength was comparable, the heat resistance of the composition containing Kraton 1107 (a styrene-isoprene block copolymer) was substantially poorer than that obtained using the styrene-butadiene copolymers of the present invention. Further, while the Kraton G1652 containing adhesive possessed some superior properties, the economic considerations involved together with the overall satisfactory properties of compositions prepared with the Stereon 840A, make these latter compositions the preferred adhesives for use herein.

Now that the preferred embodiments of the present invention have been described in detail, various modifications and improvements thereon will become readily apparent to those skilled in the art. Accordingly, the spirit and scope of the present invention is to be limited only by the appended claims, and not by the foregoing disclosure.

We claim:

1. A disposable article of the multi-line construction comprising at least one polyethylene or polypropylene substrate bonded to at least one tissue, non-woven, polyethylene or polypropylene substrate using a hot melt pressure sensitive adhesive composition comprising:
   (a) 15 to 35% by weight of an A-B-A block or A-B-A-B-A-B multi-block copolymer containing at least 28 parts styrene per 100 parts polymer where polymer blocks A are styrene blocks and polymer block B (the B component) is butadiene or hydrogenated butadiene;
   (b) 45 to 70% by weight of a compatible tackifying resin;
   (c) 5 to 30% by weight of a plasticizing oil;
   (d) 0 to 5% by weight of a petroleum derived wax; and
   (e) 0.1 to 2% by weight of a stabilizer.

2. The disposable article of claim 1 wherein the tackifying resin is any compatible resin or mixture thereof selected from the group consisting of (1) natural and modified rosins; (2) glycerol and pentaerythritol esters of natural and modified rosins; (3) copolymers and terpolymers of natured terpenes; (4) polyterpene resins having a softening point, as determined by ASTM method E28-58T, of from about 80° to 150° C.; (5) phenolic modified terpene resins and hydrogenated derivatives thereof; (6) aliphatic petroleum hydrocarbon resins having a Ball and Ring softening point of from about 70° to 135° C.; (7) aromatic petroleum hydrocarbon resins and the hydrogenated derivatives thereof; and (8) alicyclic petroleum hydrocarbon resins and the hydrogenated derivatives thereof.

3. The disposable article of claim 1 selected from the group consisting of diapers, sanitary napkins and bed pads.

4. A disposable article of the multi-line type construction comprising at least one polyethylene or polypropylene substrate bonded to at least one tissue, non-woven, polyethylene or polypropylene substrate using a hot melt pressure sensitive adhesive composition comprising:
   (a) 15 to 35% by weight of an A-B-A-B-A-B- multi-block copolymer wherein the A component is styrene and the B component is butadiene and wherein the styrene component is present in an amount of at least 35 parts per 100 parts of the copolymer;
   (b) 45 to 70% by weight of a compatible tackifying resin;

(c) 5 to 30% by weight of a plasticizing oil;
(d) 0 to 5% by weight of a petroleum derived wax; and
(e) 0.1 to 2% by weight of a stabilizer.

5. The disposable article of claim 4 wherein the block copolymer comprises 57 parts butadiene and 43 parts styrene.

6. The disposable article of claim 4 wherein the tackifying resin is any compatible resin or mixture thereof selected from the group consisting of (1) natural and modified rosins; (2) glycerol and pentaerythritol esters of natural and modified rosins; (3) copolymers and terpolymers of natured terpenes; (4) polyterpene resins having a softening point, as determined by ASTM method E28-58T, of from about 80° to 150° C. (5) phenolic modified terpene resins and hydrogenated derivatives thereof; (6) aliphatic petroleum hydrocarbon resins having a Ball and Ring softening point of from about 70° to 135° C.; (7) aromatic petroleum hydrocarbon resins and the hydrogenated derivatives thereof; and (8) alicyclic petroleum hydrocarbon resins and the hydrogenated derivatives thereof.

7. The disposable article of claim 6 wherein the tackifying resin is a modified terpene resin having a Ring and Ball softening part of about 100°-120° C.

8. The disposable article of claim 6 wherein the tackifying resin is an aromatic petroleum hydrocarbon resin or hydrogenated derivative thereof.

9. The disposable article of claim 4 selected from the group consisting of diapers, sanitary napkins and bed pads.

10. A disposable diaper produced using a multi-line type construction comprising at least one polyethylene or polypropylene substrate bonded to at least one tissue, non-woven, polyethylene or polypropylene substrate using a hot melt pressure sensitive adhesive composition comprising:

(a) 15 to 35% by weight of an A-B-A-B-A-B- multi-block copolymer wherein the A component is styrene and the B component is butadiene and wherein the styrene component is present in an amount of at least 35 parts per 100 parts of the copolymer;
(b) 45 to 70% by weight of a compatible tackifying resin;
(c) 5 to 30% by weight of a plasticizing oil;
(d) 0 to 5% by weight of a petroleum derived wax; and
(e) 0.1 to 2% by weight of a stabilizer.

11. The disposable diaper of claim 10 wherein the block copolymer comprises 57 parts butadiene and 43 parts styrene.

12. The disposable article of claim 10 wherein the tackifying resin is any compatible resin or mixture thereof selected from the group consisting of (1) natural and modified rosins; (2) glycerol and pentaerythritol esters of natural and modified rosins; (3) copolymers and terpolymers of natured terpenes; (4) polyterpene resins having a softening point, as determined by ASTM method E28-58T, of from about 80° to 150° C. (5) phenolic modified terpene resins and hydrogenated derivatives thereof; (6) aliphatic petroleum hydrocarbon resins having a Ball and Ring softening point of from about 70° to 135° C.; (7) aromatic petroleum hydrocarbon resins and the hydrogenated derivatives thereof; and (8) alicyclic petroleum hydrocarbon resins and the hydrogenated derivatives thereof.

13. The disposable article of claim 12 wherein the tackifying resin is a modified terpene resin having a Ring and Ball softening part of about 100°-120° C.

14. The disposable article of claim 12 wherein the tackifying resin is an aromatic petroleum hydrocarbon resin or hydrogenated derivative therof.

* * * * *